United States Patent [19]

Okamoto et al.

[11] Patent Number: 5,663,464

[45] Date of Patent: Sep. 2, 1997

[54] METHOD FOR PRODUCING 1,1,1,3,3-PENTAFLUOROPROPANE

[75] Inventors: Hidekazu Okamoto; Keiichi Ohnishi, both of Yokohama, Japan

[73] Assignee: Asahi Glass Company Ltd., Tokyo, Japan

[21] Appl. No.: 632,383

[22] Filed: Apr. 10, 1996

[30] Foreign Application Priority Data

Apr. 14, 1995 [JP] Japan .................. 7-089676
Mar. 15, 1996 [JP] Japan .................. 8-059649

[51] Int. Cl.$^6$ ............................................. C07C 19/08
[52] U.S. Cl. ................................ 570/175; 570/176
[58] Field of Search .............................. 570/175, 176

[56] References Cited

U.S. PATENT DOCUMENTS 2,942,036  6/1960  Smith et al.

FOREIGN PATENT DOCUMENTS 0 347 830   12/1989   European Pat. Off.
0 611 744    8/1994   European Pat. Off.
0611744      8/1994   European Pat. Off. ........ 570/176
3009080      5/1993   WIPO ........................ 570/176
WO94/29251  12/1994   WIPO.

Primary Examiner—Alan Siegel
Attorney, Agent, or Firm—Oblon, Spivak, McClelland, Maier & Neustadt, P.C.

[57] ABSTRACT

A method for producing 1,1,1,3,3-pentafluoropropane, which comprises reducing at least one chlorofluorohydrocarbon selected from the group consisting of $CF_3CClXCClF_2$ wherein X is a H atom or a Cl atom, and $CF_3CCl=CF_2$, with hydrogen in the presence of a reduction catalyst comprising, as a first component, at least one metal selected from the group consisting of Ru, Rh, Pd and Pt, and, as a second component, at least one metal selected from the group consisting of Ni, Co, La, Re, W, Ta, Nb, Ti, Zr, Mo, Cu, Ag and Au.

19 Claims, No Drawings

METHOD FOR PRODUCING 1,1,1,3,3-PENTAFLUOROPROPANE

The present invention relates to a method for producing 1,1,1,3,3-pentafluoropropane (hereinafter referred simply as 245fa). 245fa is a hydrofluorocarbon which is useful as e.g. a blowing agent and which does not destroy the ozone layer.

As methods for producing 245fa, (1) a method of hydrogenating $CF_3CH=CF_2$ in the presence of a Pd catalyst (Izvest. Akad. Nauk S. S. S. R., Otdel. Khim. Nauk. 1960, 1412), (2) a method of reducing $CF_3CCl_2CClF_2$ with hydrogen in the presence of a Pd catalyst (U.S. Pat. No. 2,942,036), and (3) a method of reducing $CF_3CClHCClF_2$ with hydrogen in the presence of a Pd catalyst (Japanese Unexamined Patent Publication No. 246235/1994) have been known.

The method (1) has a difficulty that the starting material is not readily available on an industrial scale. In each of the methods (2) and (3), Pd is used as the reduction catalyst, but the catalytic activity for the reaction and the durability at high temperature are insufficient, and these methods are not suitable as industrial ones.

The present invention has been made to overcome such drawbacks inherent to the conventional methods, and it provides a method for producing 245fa, which comprises reducing at least one chlorofluorocarbon selected from the group consisting of $CF_3CClXCClF_2$ wherein X is a H atom or a Cl atom, and $CF_3CCl=CF_2$, with hydrogen in the presence of a reduction catalyst comprising, as a first component, at least one metal selected from the group consisting of Ru, Rh, Pd and Pt, and, as a second component, at least one metal selected from the group consisting of Ni, Co, La, Re, W, Ta, Nb, Ti, Zr, Mo, Cu, Ag and Au.

Now, the present invention will be described in detail with reference to the preferred embodiments.

Hydrogen chloride is produced as a by-product by the reaction to obtain desired 245fa by reducing at least one chlorofluorocarbon selected from the group consisting of $CF_3CClXCClF_2$ wherein X is a H atom or a Cl atom, and $CF_3CCl=CF_2$, with hydrogen in the presence of a catalyst. Therefore, the catalyst is required to have acid resistance. Accordingly, a platinum group metal catalyst or a catalyst containing a platinum group metal as the primary component is preferred. However, Pd as the most common platinum group catalyst has a low melting point and is susceptible to growth of catalyst grains by sintering, and it is thus inadequate in the heat resistance, as mentioned above.

Further, when the characteristics of the starting material to be used are taken into consideration, halogenated hydrocarbons having three carbon atoms used as the starting material in the present invention generally have large molecular sizes as compared with halogenated hydrocarbons having two carbon atoms and tend to be readily adsorbed on the catalyst surface and hardly desorbed therefrom. Therefore, in order to suppress formation of by-products such as over-reduction products, it is considered to be important to control the adsorption on the catalyst surface to a proper level.

Further, this reaction is an exothermic reaction, and if the active site density on the catalyst surface is high, the temperature in the vicinity of the active sites tends to be locally high by the heat of reaction, and if the adsorbed starting material or the reaction product is present at such sites, by-products such as over-reduction products are more likely to form. Accordingly, in order to suppress formation of by-products due to local heating on the catalyst surface, it is considered important to introduce a metal having a lower activity than the main component into the catalyst to disperse the active sites.

In view of the foregoing, an extensive study has been made to use a platinum group metal as a first component and combine therewith a proper metal of different species as a second component taking the acid resistance, the heat resistance (high melting point), the size of crystal lattice, the degree of adsorptivity, etc. into consideration and to optimize the combination, the compositional proportions, the conditions for preparation of the catalyst, etc., and as a result, a catalyst has been found which is excellent not only in the catalytic activity for the reaction but also in the durability and selectivity. Thus, the present invention has been accomplished on the basis of this discovery.

Namely, it has been found that the reduction catalyst comprising, as a first component, at least one metal selected from the group consisting of Ru, Rh, Pd and Pt, and, as a second component, at least one metal selected from the group consisting of Ni, Co, La, Re, W, Ta, Nb, Ti, Zr, Mo, Cu, Ag and Au, has high catalytic activities and high heat resistance, and by using this reduction catalyst, desired 245fa can be obtained in good yield.

In the present invention, it is preferred to use the reduction catalyst having the metals of the first and second components supported on a carrier for the purposes of increasing the effective area of the reduction catalyst, stabilizing the microstructure of active sites of the reduction catalyst and dispersing the heat of reaction of the reduction catalyst to prevent local overheating.

The carrier is not particularly limited so long as it is the one having a large specific surface area and high heat resistance. A metal oxide type carrier such as alumina or zirconia, or an active carbon type carrier such as coconut shell active carbon, is preferred. Particularly preferred is an active carbon type carrier. As the supporting method, a conventional method for preparing a noble metal catalyst can be applied. An impregnation method is preferred. The impregnation method may be conducted, for example, in such a manner that the pH of an aqueous solution of metal salts of the catalyst components is adjusted to be acidic so that the catalyst components will be adsorbed uniformly and then ions containing the metal elements of the catalyst components are adsorbed on a carrier, followed further by reduction treatment to obtain the catalyst.

The carrier may preliminarily be immersed in water such as pure water to impregnate water to the interior of fine pores, and then an aqueous solution of metal salts of the catalyst components may be impregnated. In such a case, the pH of at least one of the water to be impregnated into the interior of fine pores and the aqueous solution of the metal salts is preferably adjusted to be acidic.

The reduction treatment method may be a wet system reduction method or a gas phase reduction method. The wet system reduction method is a method wherein the carrier is immersed in an aqueous solution of metal salts of the catalyst components to have ions containing the metal elements of the catalyst components adsorbed thereon, whereupon a suitable reducing agent is added, and reduction is carried out at room temperature. The reducing agent may, for example, be formalin, hydrazine, formic acid or sodium boron hydride.

The gas phase reduction method is a method wherein ions containing metal elements of the catalyst components are adsorbed on a carrier, followed by washing with water to remove free ion components, whereupon the carrier is dried and subjected to reduction in a hydrogen stream at a relatively high temperature.

It is preferred that before using the reduction catalyst for the reduction reaction, at least a part of the metals of the catalyst components is subjected to reduction to obtain stabilized properties. Otherwise, such reduction treatment can be carried out at the same time as the starting material during the process of the reduction reaction.

The metals of the first and second components supported on the carrier may be separately supported as independent metal particles, respectively. Otherwise, they may be supported in a dispersed state in the form of particles having both metal particles coagulated. The particles having both metal particles coagulated are preferably alloyed, since the heat resistance is thereby improved, or the durability of the reduction catalyst is thereby improved. In the Examples given hereinafter, the metals of the first and second components in the reduction catalyst are believed to be alloyed.

The proportion of the second component in the reduction catalyst is preferably at least 0.01 wt %, more preferably at least 0.1 wt %, to suppress sintering, to suppress the adsorptivity of the catalyst surface or to disperse the active sites.

The upper limit of the proportion of the second component in the reduction catalyst varies depending upon the type of the metal of the second component. In a case where a Group 11 metal element such as Cu, Ag or Au is contained, the reduction activities of the catalyst will not substantially decrease even when the content of such a metal increases, and such a metal can be incorporated preferably up to 50 wt % in the reduction catalyst.

The proportion of a metal of the second component other than the Group 11 metal element is preferably controlled to be at most 50 wt %, more preferably at most 20 wt %, to effectively utilize the catalytic properties of the first component. If the content of the second component is increased beyond 50 wt %, the properties of the second component having low catalytic activities tend to be governing, whereby the catalytic activities for reaction tend to be low, such being undesirable.

When the above Group 11 metal and a metal of the second component other than the Group 11 metal are used in combination, the total proportion in the reduction catalyst is preferably up to 70 wt %, more preferably up to 50 wt %.

The lower limit of the proportion of the first component in the reduction catalyst varies depending upon the type of the metal of the second component contained, but is preferably 30 wt %, more preferably 50 wt %.

Metals of the first component selected from the group consisting of Ru, Rh, Pd and Pt may be used alone or in combination as a mixture of two or more of them. Also with respect to metals of the Second component, metals selected from the group consisting of Ni, Co, La, Re, W, Ta, Nb, Ti, Zr, Mo, Cu, Ag and Au, may be used alone or in combination as a mixture of two or more of them. Preferred as the second component is at least one member selected from the group consisting of Cu, Ag and Au. A preferred combination of two or more members of the second component may, for example, be a combination of at least one member selected from the group consisting of Cu, Ag and Au and at least one member selected from the group consisting of Ni, Co, La, Re, W, Ta, Nb, Ti, Zr and Mo, or a combination of two or more members selected from the group consisting of Cu, Ag and Au.

Metals other than the above described metals of the first and second components may be incorporated so long as the performance expected by the reduction catalyst in the present invention is not impaired.

The pressure for the reduction reaction may be atmospheric pressure or a pressure above atmospheric pressure.

The temperature for the reduction reaction is preferably from 0° to 450° C., more preferably from 50° to 300° C. The reduction reaction is preferably conducted in a gas phase within this temperature range, from the viewpoint of the reaction selectivity and the useful life of the catalyst.

The molar ratio of hydrogen to be supplied to the chlorofluorohydrocarbon to be reduced by the reduction reaction can be varied within a wide range. Usually, it is preferred to react hydrogen in an amount of from 1 to 10 times the stoichiometrical amount to the chlorofluorohydrocarbon. The contact time for the reduction reaction is usually from 0.1 to 300 seconds, preferably from 2 to 60 seconds, although it may depends also on the amount of the catalyst, and the linear velocity of gas is preferably from 2 to 100 cm/sec.

For the reduction reaction, a batch reaction or a continuous reaction wherein the starting material is continuously supplied to a reactor, and the reaction product is continuously withdrawn from the reactor, may be employed. The continuous reaction is preferred.

The starting material chlorofluorohydrocarbon is selected from the group consisting of $CF_3CClXCClF_2$ wherein X is a H atom or a Cl atom, which represents $CF_3CHClCClF_2$ or $CF_3CCl_2CClF_2$, and $CF_3CCl=CF_2$. These chlorofluorohydrocarbons may be used alone or in combination as a mixture of two or more of them.

When two or more of the above chlorofluorohydrocarbons to be used as the starting material, are produced in combination, as described hereinafter, the two or more chlorofluorohydrocarbons produced in combination are preferably supplied as they are to the reduction reaction.

Each of the starting materials $CF_3CHClCClF_2$, $CF_3CCl_2CClF_2$ and $CF_3CCl=CF_2$ can be obtained by liquid phase chlorofluorination, by chlorine and hydrogen fluoride, of at least one halogenated propene selected from the group consisting of $CCl_3CH=CCl_2$, $CCl_3CCl=CHCl$ and $CF_3CCl=CHCl$. Under usual conditions, two or more of the above stating materials are produced in combination by the liquid phase chlorofluorination reaction of the above halogenated propene.

Each of the starting materials $CF_3CH_{ClCCF2}$, $CF_3CCl_2CClF_2$ and $CF_3CCl=CF_2$ can also be obtained by liquid phase fluorination of $CCl_3CCl=CCl_2$ by hydrogen fluoride. Under usual conditions, two or more of the above starting materials will be produced in combination by the liquid phase fluorination reaction.

The above liquid phase chlorofluorination and the liquid phase fluorination are preferably conducted in the presence of a catalyst which contains a halide such as chloride, a fluoride or a chlorofluoride, of at least one element selected from the group consisting of Sb, Nb, Ta and Sn, as an essential component. Specifically, preferred is a catalyst containing a chloride, a fluoride or a chlorofluoride, such as $SbF_5$, $SbCl_5$, $SbCl_2F_3$, $NbCl_5$, $NbClF_4$, $NbF_5$, $TaF_5$, $TaCl_5$, $TaClF_4$, $SnCl_4$ or $SnClF_3$, as the essential component. The amount of the catalyst is not particularly limited.

The liquid phase chlorofluorination reaction and the liquid phase fluorination reaction are preferably carried out under atmospheric pressure or elevated pressure within a temperature range of from 0° to 200° C., more preferably from 20° to 150° C. The reaction is usually conducted in the reaction starting material and the reaction product. However, the reaction may be carried out in a solvent for reaction other than the reaction starting material and the reaction product. The solvent to be used in such a case is not particularly limited so long as it is capable of dissolving the starting material and the solvent itself is more hardly fluorinated or chlorinated than the starting material.

The molar ratios of hydrogen fluoride and chlorine to the starting material to be chlorofluorinated by the liquid phase chlorofluorination reaction, are not particularly limited so long as they are at least the stoichiometric amounts. In view of the reactor efficiency and the loss due to recovery of hydrogen fluoride and chlorine, they are preferably within a range of from 1 to 10 mol times, more preferably from 1 to 5 mol times, relative to the stoichiometric amounts. Hydrogen fluoride and chlorine may preliminarily be charged prior to the reaction, or may be blown into the liquid phase at the time of the reaction. The reaction pressure is usually from 0 to 20 kg/cm$^2$ (gauge pressure), but may vary depending upon e.g. the type of the solvent for reaction.

The molar ratio of hydrogen fluoride supplied to the starting material to be fluorinated by the liquid phase fluorination reaction, is not particularly limited so long as it is at least the stoichiometric amount. In view of the reactor efficiency and the loss due to recovery of hydrogen fluoride, it is preferably within a range of from 1 to 10 mol times, more preferably from 1 to 5 mol times, relative to the stoichiometric amount. Hydrogen fluoride may be preliminarily charged before the reaction, or may be blown into the liquid phase at the time of the reaction. The reaction pressure is usually from 0 to 20 kg/cm$^2$ (gauge pressure), but may vary depending upon e.g. the type of the solvent for reaction.

Now, the present invention will be described in further detail with reference to Examples. However, it should be understood that the present invention is by no means restricted to such specific Examples. In the following description, Preparation Examples 1 to 20 represent examples for preparation of reduction catalysts, and Examples 1 to 20 represent working examples of the present invention, and Examples 27 to 34 represent comparative examples. Further, "%" in Tables 1 to 6 means "mol %".

PREPARATION EXAMPLE 1

Coconut shell active carbon was immersed in water having the pH adjusted to be acidic with hydrochloric acid, to impregnate water into the interior of fine pores. To this active carbon, an aqueous solution having palladium chloride and copper sulfate dissolved in a weight ratio of the respective metal components of 90:10 so that the total weight of the metal components to the weight of active carbon became 0.5 wt %, was gradually dropped to have the ion components adsorbed on the active carbon. The active carbon having the metal components thus supported thereon, was washed with pure water and then dried at 150° C. for 5 hours. Then, it was dried in nitrogen at 550° C. for 4 hours, whereupon hydrogen was introduced, and it was maintained and reduced for 5 hours at 250° C.

PREPARATION EXAMPLE 2

A catalyst was prepared in the same manner as in Preparation Example 1 except that palladium chloride was changed to palladium sulfate, copper sulfate was changed to silver nitrate, and reduction by hydrogen was changed to reduction by hydrazine at room temperature.

PREPARATION EXAMPLE 3

A catalyst was prepared in the same manner as in Preparation Example 1 except that copper sulfate was changed to chloroauric acid.

PREPARATION EXAMPLE 4

A catalyst was prepared in the same manner as in Preparation Example 1 except that instead of palladium chloride and copper sulfate, palladium chloride, potassium tungstate and chloroauric acid were used in the weight ratio of the respective metal components (Pd:W:Au) of 90:2:8.

PREPARATION EXAMPLE 5

A catalyst was prepared in the same manner as in Preparation Example 1 except that instead of palladium chloride and copper sulfate, palladium chloride, potassium perrhenate and chloroauric acid were used in a weight ratio of the respective metal components (Pd:Re:Au) of 90:1:9.

PREPARATION EXAMPLE 6

A catalyst was prepared in the same manner as in Preparation Example 1 except that instead of palladium chloride and copper sulfate, palladium chloride, ammonium molybdate and chloroauric acid were used in a weight ratio of the respective metal components of 90:1:9.

PREPARATION EXAMPLE 7

A catalyst was prepared in the same manner as in Preparation Example 1 except that instead of palladium chloride and copper sulfate, rhodium sulfate and silver nitrate were used in a weight ratio of the respective metal components of 90:10.

PREPARATION EXAMPLE 8

A catalyst was prepared in the same manner as in Preparation Example 1 except that instead of palladium chloride and copper sulfate, rhodium chloride, lanthanum chloride and chloroauric acid were used in a weight ratio of the respective metal components of 90:1:9.

PREPARATION EXAMPLE 9

A catalyst was prepared in the same manner as in Preparation Example 1 except that instead of palladium chloride and copper sulfate, rhodium chloride, cobalt chloride and copper sulfate were used in a weight ratio of the respective metal components of 45:45:10.

PREPARATION EXAMPLE 10

A catalyst was prepared in the same manner as in Preparation Example 1 except that instead of palladium chloride and copper sulfate, rhodium sulfate, titanium tetrachloride and silver nitrate were used in a weight ratio of the respective metal components of 90:1:9.

PREPARATION EXAMPLE 11

A catalyst was prepared in the same manner as in Preparation Example 1 except that instead of palladium chloride and copper sulfate, rhodium chloride, zirconium chloride and chloroauric acid were used in a weight ratio of the respective metal components of 90:1:9.

PREPARATION EXAMPLE 12

A catalyst was prepared in the same manner as in Preparation Example 1 except that palladium chloride was changed to chloroplatinic acid, and copper sulfate was changed to chloroauric acid.

PREPARATION EXAMPLE 13

A catalyst was prepared in the same manner as in Preparation Example 1 except that instead of palladium chloride and copper sulfate, palladium chloride, nickel chloride and copper sulfate were used in a weight ratio of the respective metal components of 45:45:10.

PREPARATION EXAMPLE 14

A catalyst was prepared in the same manner as in Preparation Example 1 except that instead of palladium chloride and copper sulfate, palladium sulfate, iridium chloride and silver nitrate were used in a weight ratio of the respective metal components of 90:1:9.

PREPARATION EXAMPLE 15

A catalyst was prepared in the same manner as in Preparation Example 1 except that instead of palladium chloride and copper sulfate, palladium chloride, tantalum pentachloride and chloroauric acid were used in a weight ratio of the respective metal components of 90:1:9.

PREPARATION EXAMPLE 16

A catalyst was prepared in the same manner as in Preparation Example 1 except that instead of palladium chloride and copper sulfate, ruthenium chloride, niobium pentachloride and chloroauric acid were used in a weight ratio of the respective metal components of 90:1:9.

PREPARATION EXAMPLE 17

A catalyst was prepared in the same manner as in Preparation Example 1 except that copper sulfate was not used.

PREPARATION EXAMPLE 18

A catalyst was prepared in the same manner as in Preparation Example 1 except that instead of palladium chloride and copper sulfate, only ruthenium chloride was used.

PREPARATION EXAMPLE 19

A catalyst was prepared in the same manner as in Preparation Example 1 except that instead of palladium chloride and copper sulfate, only rhodium chloride was used.

PREPARATION EXAMPLE 20

A catalyst was prepared in the same manner as in Preparation Example 1 except that instead of palladium chloride and copper sulfate, only chloroplatinic acid was used.

EXAMPLE 1

A U-shaped Inconel 600 reactor tube having an inner diameter of ½ inch and a length of 100 cm, packed with 100 ml of the catalyst prepared in Preparation Example 1, was immersed in a salt bath furnace of 200° C. Hydrogen and $CF_3CClHCClF_2$ were introduced into the above reactor tube in a molar ratio of 3:1. The flow rates of the hydrogen and the starting material were 300 ml/min and 100 ml/min, respectively. The contact time was 15 seconds. The reaction product was collected in a trap cooled to −78° C. After removing an acid content from the collected product, the composition was analyzed by gas chromatography and $^{19}$F-NMR. As a result, the main product was confirmed to be 245fa. The reaction results upon expiration of 6 hours after initiation of the reaction are shown in the table given hereinafter.

EXAMPLE 2

The reduction reaction was carried out in the same manner as in Example 1 except that a mixture of $CF_3CClHCClF_2$ and $CFCCl=CF_2$ (molar ratio of 95:5) was used. The reaction results upon expiration of 6 hours after initiation of the reaction are shown in the table.

EXAMPLE 3

The reduction reaction was carried out in the same manner as in Example 1 except that a mixture of $CF_3CClHCClF_2$, $CFCCl=CP_2$ and $CF_3CCl_2CClF_2$ (molar ratio of 88:11:1) was used. The reaction results upon expiration of 6 hours after initiation of the reaction are shown in the table.

EXAMPLES 4 TO 19

A U-shaped Inconel 600 reactor tube having an inner diameter of ½ inch and a length of 100 cm, packed with 100 ml of the catalyst prepared in one of Preparation Examples 1 to 16, was immersed in a salt bath furnace of 200° C.

Hydrogen, and a mixture of $CF_3CClHCClF_2$, $CF_3CCl=CF_2$ and $CF_3CCl_2CClF_2$ (molar ratio of 82:15:3), were introduced into the above reactor tube in a molar ratio of 3:1. The flow rates of the hydrogen and the mixture of starting materials were 300 ml/min and 100/min, respectively. The contact time was 15 seconds. The reaction product was collected in a trap cooled to −78° C. After removing an acid content from the collected product, the composition was analyzed by gas chromatography and $^{19}$F-NMR. AS a result, the main product was confirmed to be 245fa. The reaction results upon expiration of 500 hours after initiation of the reaction are shown in the table.

EXAMPLE 20

A U-shaped Inconel 600 reactor tube having an inner diameter of ½ inch and a length of 100 cm, packed with 100 ml of the catalyst prepared in Preparation Example 1, was immersed in a salt bath furnace of 200° C.

Hydrogen, and a mixture of $CF_3CClHCClF_2$ and $CF_3CCl=CF_2$ (molar ratio of 65:35), were introduced into the above reactor tube in a molar ratio of 3:1. The flow rates of the hydrogen and the mixture were 300 ml/min and 100/min, respectively. The contact time was 15 seconds. The reaction product was collected in a trap cooled to −78° C. After removing an acid content from the collected product, the composition was analyzed by gas chromatography and $^{19}$F-NMR. As a result, the main product was confirmed to be 245fa. The reaction results upon expiration of 6 hours after initiation of the reaction are shown in the table.

EXAMPLE 21

A reduction reaction was carried out in the same manner as in Example 20 except that a mixture of $CF_3CClHCClF_2$ and $CF_2CCl=CF_2$ (molar ratio of 83:17) was used. The reaction results upon expiration of 6 hours after initiation of the reaction are shown in the table.

EXAMPLE 22

A U-shaped Inconel 600 reactor tube having an inner diameter of ½ inch and a length of 100 cm, packed with 100 ml of the catalyst prepared in Preparation Example 1, was immersed in a salt bath furnace of 200° C.

Hydrogen, and a mixture of $CF_3CClHCClF_2$ and $CF_3CCl=CF_2$ (molar ratio of 87:13) were introduced into the above reactor tube in a molar ratio of 3:1. The flow rates of the hydrogen and the mixture were 300 ml/min and 100 ml/min, respectively. The contact time was 15 seconds. The reaction product was collected in a trap cooled to −78° C. After removing an acid content from the collected product, the composition was analyzed by gas chromatography and 19F-NMR. As a result, the main product was confirmed to be 245fa. The reaction results upon expiration of 6 hours after initiation of the reaction are shown in the table.

EXAMPLE 23

A reduction reaction was carried out in the same manner as in Example 20 except that the molar ratio of the mixture of $CF_3CClHCClF_2$ and $CF_3CCl=CF_2$ was changed to 60:40. The reaction results upon expiration of 6 hours after initiation of the reaction are shown in the table.

EXAMPLE 24

A reduction reaction was carried out in the same manner as in Example 20 except that the molar ratio of the mixture of $CF_3CClHCClF_2$ and $CF_3CCl=CF_2$ was changed to 60:40. The reaction results upon expiration of 6 hours after initiation of the reaction are shown in the table.

EXAMPLE 25

A reduction reaction was carried out in the same manner as in Example 1 except that $CF_3CCl=CF_2$ was used instead of $CF_3CClHCClF_2$. The reaction results upon expiration of 6 hours after initiation of the reaction are shown in the table.

EXAMPLE 26

A reduction reaction was carried out in the same manner as in Example 1 except that $CF_3CCl_2CClF_2$ was used instead of $CF_3CClHCClF_2$. The reaction results upon expiration of 6 hours after initiation of the reaction are shown in the table.

EXAMPLES 27 AND 28

A reduction reaction was carried out in the same manner as in Example 4 except that the catalyst prepared in Preparation Example 17 or 18 and a mixture of $CFCClHCClF_2$, $CF_3CCl=CF_2$ and $CF_3CCl_2CClF_2$ (molar ratio of 82:15:3) were used. The reaction results upon expiration of 500 hours after initiation of the reaction are shown in the table.

EXAMPLE 29

A reduction reaction was carried out in the same manner as in Example 1 except that the catalyst prepared in Preparation Example 17 was used. The reaction results upon expiration of 500 hours after initiation of the reaction are shown in the table.

EXAMPLE 30

A reduction reaction was carried out in the same manner as in Example 2 except that the catalyst prepared in Preparation Example 17 was used. The reaction results upon expiration of 500 hours after initiation of the reaction are shown in the table.

EXAMPLE 31

A reduction reaction was carried out in the same manner as in Example 1 except that the catalyst prepared in Preparation Example 17 and $CF_3CCl=CF_2$ were used. The reaction results upon expiration of 500 hours after initiation of the reaction are shown in the table.

EXAMPLE 32

A reduction reaction was carried out in the same manner as in Example 1 except that the catalyst prepared in Preparation Example 17 and $CF_3CCl_2CClF_2$ were used. The reaction results upon expiration of 500 hours after initiation of the reaction are shown in the table.

EXAMPLE 33

A reduction reaction was carried out in the same manner as in Example 4 except that the catalyst prepared in Preparation Example 19 was used. The reaction results upon expiration of 500 hours after initiation of the reaction are shown in the table.

EXAMPLE 34

A reduction reaction was carried out in the same manner as in Example 4 except that the catalyst prepared in Preparation Example 20 was used. The reaction results upon expiration of 500 hours after initiation of the reaction are shown in the table.

The chlorofluorohydrocarbons used as the starting materials in the above Examples 1 to 34 were obtained by liquid phase fluorination of $CCl_3CCl=CCl_2$ with hydrogen fluoride.

TABLE 1

| Example No. | 1 | 2 | 3 | 4 | 5 | 6 |
|---|---|---|---|---|---|---|
| Catalyst composition | Pd—Cu | Pd—Cu | Pd—Cu | Pd—Cu | Pd—Ag | Pd—Au |
| Conversion (%) | 95 | 96 | 97 | 97 | 97 | 98 |
| Selectively (%) | | | | | | |
| $CF_3CH_2CHF_2$ | 97 | 98 | 96 | 96 | 95 | 96 |
| Other | 3 | 2 | 4 | 4 | 5 | 4 |

TABLE 2

| Example No. | 7 | 8 | 9 | 10 | 11 |
|---|---|---|---|---|---|
| Catalyst composition | Pd—W—Au | Pd—Re—Au | Pd—Mo—Au | Rh—Ag | Rh—La—Au |
| Conversion (%) | 97 | 96 | 94 | 95 | 95 |
| Selectively (%) | | | | | |
| $CF_3CH_2CHF_2$ | 96 | 95 | 96 | 94 | 95 |
| Other | 4 | 5 | 4 | 6 | 5 |

TABLE 3

| Example No. | 12 | 13 | 14 | 15 | 16 |
|---|---|---|---|---|---|
| Catalyst composition | Rh—Co—Cu | Rh—Ti—Ag | Rh—Zr—Au | Pt—Au | Pd—Ni—Cu |
| Conversion (%) | 95 | 95 | 96 | 96 | 97 |
| Selectively (%) | | | | | |
| $CF_3CH_2CHF_2$ | 94 | 95 | 96 | 96 | 97 |
| Other | 6 | 5 | 4 | 4 | 3 |

TABLE 4

| Example No. | 17 | 18 | 19 | 20 | 21 | 22 |
|---|---|---|---|---|---|---|
| Catalyst composition | Pd—Ir—Ag | Pd—Ta—Au | Ru—Nb—Au | Pd—Cu | Pd—Cu | Pd—Cu |
| Conversion (%) | 96 | 96 | 93 | 98 | 97 | 97 |
| Selectively (%) | | | | | | |
| $CF_3CH_2CHF_2$ | 96 | 96 | 93 | 94 | 95 | 95 |
| Other | 4 | 4 | 7 | 6 | 5 | 5 |

TABLE 5

| Example No. | 23 | 24 | 25 | 26 |
|---|---|---|---|---|
| Catalyst composition | Pd—Cu | Pd—Cu | Pd—Cu | Pd—Cu |
| Conversion (%) | 98 | 98 | 98 | 97 |
| Selectively (%) | | | | |
| $CF_3CH_2CHF_2$ | 95 | 95 | 95 | 94 |
| Other | 5 | 5 | 5 | 6 |

TABLE 6

| Example No. | 27 | 28 | 29 | 30 | 31 | 32 | 33 | 34 |
|---|---|---|---|---|---|---|---|---|
| Catalyst composition | Pd | Ru | Pd | Pd | Pd | Pd | Rh | Pt |
| Conversion (%) | 60 | 41 | 62 | 58 | 56 | 50 | 50 | 65 |
| Selectively (%) | | | | | | | | |
| $CF_3CH_2CHF_2$ | 92 | 81 | 90 | 89 | 92 | 85 | 90 | 80 |
| Other | 8 | 19 | 10 | 11 | 8 | 15 | 10 | 20 |

The present invention provides an effect such that 245fa which used to be difficult to produce on an industrial scale, can readily be produced in good yield.

What is claimed is:

1. A method for producing 1,1,1,3,3-pentafluoropropane, which comprises reducing at least one chlorofluorohydrocarbon selected from the group consisting of $CF_3CClXClF_2$ wherein X is a H atom of a Cl atom, and $CF_3CCl=CF_2$, with hydrogen in the presence of a reduction catalyst comprising, as a first component, at least one metal selected from the group consisting of Ru, Rh, Pd and Pt, and, as a second component, at least one metal selected from the group consisting of Ni, Co, La, Re, W, Ta, Nb, Ti, Zr, Mo, Cu, Ag and Au,
wherein said reduction catalyst is supported on a carrier.

2. The method according to claim 1, wherein the proportion of the second component in the reduction catalyst is from 0.01 to 70 wt%.

3. The method according to claim 1, wherein the proportion of the second component in the reduction catalyst is from 0.1 to 50 wt %.

4. The method according to claim 1, wherein the first component of the reduction catalyst is Pd, and the second component is at least one member selected from the group consisting of Cu, Ag and Au.

5. The method according to claim 1, wherein the first component of the reduction catalyst is Rh, and the second component is Ag.

6. The method according to claim 1, wherein the first component of the reduction catalyst is Pt, and the second component is Au.

7. The method according to claim 1, wherein the second component of the reduction catalyst is one member selected from the group consisting of Cu, Ag and Au and one member selected from the group consisting of Ni, Co, La, Re, W, Ta, Nb, Ti, Zr and Mo.

8. The method according to claim 1, wherein the first component of the reduction catalyst is Pd, and the second component is one member selected from the group consisting of Cu, Ag and Au and one member selected from the group consisting of Ni, Co, La, Re, W, Ta, Nb, Ti, Zr and Mo.

9. The method according to claim 1, wherein the first component of the reduction catalyst is Rh, and the second component is one member selected from the group consisting of Cu, Ag and Au and one member selected from the group consisting of Ni, Co, La, Re, W, Ta, Nb, Ti, Zr and Mo.

10. The method according to claim 1, wherein the first component of the reduction catalyst is Ru, and the second component is one member selected from the group consisting of Cu, Ag and Au and one member selected from the group consisting of Ni, Co, La, Re, W, Ta, Nb, Ti, Zr and Mo.

11. The method according to claim 1, wherein the first component of the reduction catalyst is Ru, and the second component is Au and Nb.

12. The method according to claim 1, wherein the chlorofluorohydrocarbon is $CF_3CClHCClF_2$.

13. The method according to claim 1, wherein the chlorofluorohydrocarbon is $CF_3CCl=CF_2$.

14. The method according to claim 1, wherein the chlorofluorohydrocarbon is a mixture of $CF_3CClHCClF_2$ and $CF_3CCl=CF_2$.

15. The method according to claim 1, wherein the chlorofluorohydrocarbon is a mixture of $CF_3CClHCClF_2$, $CF_3CCl_2CClF_2$ and $CF_3CCl=CF_2$.

16. The method according to claim 1, wherein the amount of hydrogen supplied is from 1 to 10 times the stoichiometric amount to the chlorofluorohydrocarbon.

17. The method according to claim 1, wherein the temperature for the reduction is from 0° to 450° C.

18. The method according to claim 1, wherein the contact time for the reduction is from 0.1 to 300 seconds.

19. The method according to claim 1, wherein the reduction is carried out in a gas phase.

* * * * *